United States Patent
Smisson, III et al.

(10) Patent No.: US 8,057,521 B2
(45) Date of Patent: Nov. 15, 2011

(54) SURGICAL STABILIZATION SYSTEM

(75) Inventors: Hugh F. Smisson, III, Macon, GA (US); David C. Field, Snellville, GA (US); Paul Gombar, Winder, GA (US); Rich Griffith, Covington, GA (US)

(73) Assignee: Southern Spine, LLC, Macon, GA (US)

( * ) Notice: Subject to any disclaimer, the term of this patent is extended or adjusted under 35 U.S.C. 154(b) by 772 days.

(21) Appl. No.: 11/422,199

(22) Filed: Jun. 5, 2006

(65) Prior Publication Data
US 2006/0293670 A1  Dec. 28, 2006

Related U.S. Application Data

(60) Provisional application No. 60/687,490, filed on Jun. 3, 2005.

(51) Int. Cl.
*A61B 17/56* (2006.01)
*A61B 17/58* (2006.01)
*A61B 17/80* (2006.01)
*A61B 17/88* (2006.01)
*A61F 2/30* (2006.01)

(52) U.S. Cl. .............. 606/288; 606/71; 606/281

(58) Field of Classification Search .......... 606/70, 606/71, 280, 283–284, 286, 289, 295, 296, 606/298, 299
See application file for complete search history.

(56) References Cited

U.S. PATENT DOCUMENTS

| | | |
|---|---|---|
| 4,957,496 A | 9/1990 | Schmidt |
| 4,957,497 A * | 9/1990 | Hoogland et al. ........... 606/71 |
| 5,403,136 A | 4/1995 | Mathys |
| 5,456,685 A | 10/1995 | Huebner |
| 5,492,442 A | 2/1996 | Lasner |
| 5,549,612 A | 8/1996 | Yapp |
| 5,562,672 A | 10/1996 | Huebner |
| 5,571,139 A | 11/1996 | Jenkins, Jr. |
| 5,601,553 A | 2/1997 | Trebing et al. |
| 5,766,254 A | 6/1998 | Gelbard |
| 5,792,142 A | 8/1998 | Galitzer |
| 5,797,914 A | 8/1998 | Leibinger |
| 5,843,082 A | 12/1998 | Yuan |
| 5,871,486 A | 2/1999 | Huebner |
| 5,876,402 A * | 3/1999 | Errico et al. ........... 606/287 |
| 5,876,435 A | 3/1999 | Swords et al. |
| 5,925,048 A | 7/1999 | Ahmad |
| 5,951,558 A | 9/1999 | Fiz |
| 6,030,162 A | 2/2000 | Huebner |

(Continued)

FOREIGN PATENT DOCUMENTS
FR  2855391 A1  12/2004
(Continued)

*Primary Examiner* — Thomas C. Barrett
*Assistant Examiner* — David Bates
(74) *Attorney, Agent, or Firm* — Sutherland Asbill & Brennan LLP

(57) ABSTRACT

The present invention discloses a device and method to establish and maintain bone stabilization and enhance post-operative healing in a surgical site, such as the cervical spine of a patient, with reduced risk of erosion or other injury to adjacent anatomic structures from extrusion of surgical fasteners, such as bone screws. The surgical stabilization system according to the present invention provides for the secure plating of structures such as adjacent vertebral bodies with allowance for selective postoperative motion of the surgical fasteners used to secure the plate. Such motion imparts benefit from increased translational response and remodeling in the course of bone healing, thus resulting in strengthened fusion.

24 Claims, 7 Drawing Sheets

U.S. PATENT DOCUMENTS

| | | | |
|---|---|---|---|
| 6,083,227 | A | 7/2000 | Saurat |
| 6,139,550 | A * | 10/2000 | Michelson ............. 606/70 |
| 6,166,666 | A | 12/2000 | Kadyk |
| 6,193,721 | B1 | 2/2001 | Michelson |
| 6,224,602 | B1 | 5/2001 | Hayes |
| 6,293,949 | B1 | 9/2001 | Justis |
| 6,312,431 | B1 | 11/2001 | Asfora |
| 6,331,179 | B1 * | 12/2001 | Freid et al. ............. 606/279 |
| 6,364,880 | B1 | 4/2002 | Michelson |
| 6,383,186 | B1 | 5/2002 | Michelson |
| 6,398,783 | B1 | 6/2002 | Michelson |
| 6,413,259 | B1 | 7/2002 | Lyons et al. |
| 6,416,528 | B1 | 7/2002 | Michelson |
| 6,428,542 | B1 | 8/2002 | Michelson |
| 6,454,770 | B1 | 9/2002 | Klaue |
| 6,454,771 | B1 | 9/2002 | Michelson |
| 6,458,133 | B1 | 10/2002 | Lin |
| 6,503,252 | B2 | 1/2003 | Hansson |
| 6,508,820 | B2 | 1/2003 | Bales |
| 6,527,776 | B1 | 3/2003 | Michelson |
| 6,533,786 | B1 | 3/2003 | Needham |
| 6,585,740 | B2 | 7/2003 | Schlapfer et al. |
| 6,589,245 | B1 | 7/2003 | Weiler et al. |
| 6,592,586 | B1 | 7/2003 | Michelson |
| 6,616,666 | B1 | 9/2003 | Michelson |
| 6,635,059 | B2 | 10/2003 | Randall et al. |
| 6,652,525 | B1 | 11/2003 | Assaker |
| 6,712,818 | B1 | 3/2004 | Michelson |
| 6,736,820 | B2 | 5/2004 | Biedermann et al. |
| 6,766,781 | B2 | 7/2004 | Penzel |
| 6,793,658 | B2 | 9/2004 | LeHuec et al. |
| D499,692 | S | 12/2004 | Brown |
| 6,916,320 | B2 | 7/2005 | Michelson |
| 6,926,718 | B1 | 8/2005 | Michelson |
| 6,936,050 | B2 | 8/2005 | Michelson |
| 6,936,051 | B2 | 8/2005 | Michelson |
| 6,969,390 | B2 | 11/2005 | Michelson |
| 7,001,387 | B2 | 2/2006 | Farris et al. |
| 7,041,105 | B2 | 5/2006 | Michelson |
| 7,044,952 | B2 | 5/2006 | Michelson |
| 7,063,701 | B2 | 6/2006 | Michelson |
| 7,063,702 | B2 | 6/2006 | Michelson |
| 7,074,221 | B2 | 7/2006 | Michelson |
| 7,077,844 | B2 | 7/2006 | Michelson |
| 7,094,239 | B1 | 8/2006 | Michelson |
| 7,097,645 | B2 | 8/2006 | Michelson |
| 7,112,202 | B2 | 9/2006 | Michelson |
| 7,112,222 | B2 | 9/2006 | Fraser et al. |
| 7,118,573 | B2 | 10/2006 | Michelson |
| 7,137,984 | B2 | 11/2006 | Michelson |
| 7,186,256 | B2 | 3/2007 | Michelson |
| 7,195,633 | B2 | 3/2007 | Medoff et al. |
| 7,207,994 | B2 | 4/2007 | Vlahos |
| 7,273,481 | B2 | 9/2007 | Lombardo et al. |
| 7,306,605 | B2 | 12/2007 | Ross |
| 7,527,641 | B2 * | 5/2009 | Suh ............. 606/289 |
| 2002/0016594 | A1 | 2/2002 | Schlapfer et al. |
| 2002/0183754 | A1 | 12/2002 | Michelson |
| 2004/0006345 | A1 | 1/2004 | Vlahos et al. |
| 2004/0044345 | A1 | 3/2004 | DeMoss et al. |
| 2004/0181229 | A1 | 9/2004 | Michelson |
| 2004/0215195 | A1 | 10/2004 | Shipp et al. |
| 2004/0220571 | A1 | 11/2004 | Assaker et al. |
| 2004/0236334 | A1 | 11/2004 | Michelson |
| 2004/0236335 | A1 | 11/2004 | Michelson |
| 2004/0239127 | A1 | 12/2004 | Lodwick, Jr. |
| 2004/0243129 | A1 | 12/2004 | Moumene et al. |
| 2005/0021036 | A1 | 1/2005 | Whitmore et al. |
| 2005/0027297 | A1 | 2/2005 | Michelson |
| 2005/0027298 | A1 | 2/2005 | Michelson |
| 2005/0033433 | A1 | 2/2005 | Michelson |
| 2005/0038436 | A1 | 2/2005 | Michelson |
| 2005/0038438 | A1 | 2/2005 | Anderson et al. |
| 2005/0059971 | A1 | 3/2005 | Michelson |
| 2005/0187552 | A1 | 8/2005 | Michelson |
| 2005/0228388 | A1 | 10/2005 | Brodke et al. |
| 2006/0106389 | A1 | 5/2006 | Reber et al. |
| 2006/0135960 | A1 | 6/2006 | Munro |
| 2006/0149263 | A1 | 7/2006 | Newcomb et al. |
| 2006/0149265 | A1 | 7/2006 | James et al. |
| 2006/0173462 | A1 | 8/2006 | Kay |
| 2006/0195099 | A1 | 8/2006 | Bottlang |
| 2007/0053765 | A1 | 3/2007 | Warnick et al. |
| 2007/0083206 | A1 | 4/2007 | Du |
| 2008/0015595 | A1 | 1/2008 | Renard et al. |
| 2008/0249579 | A1 | 10/2008 | Taylor |
| 2009/0287257 | A1 * | 11/2009 | Hagen ............. 606/289 |
| 2010/0222814 | A1 * | 9/2010 | Freid et al. ............. 606/246 |

FOREIGN PATENT DOCUMENTS

WO   WO2004/006792   1/2004

* cited by examiner

SURGICAL STABILIZATION SYSTEM

CROSS REFRENCE TO RELATED APPLICATION

This application claims the priority benefit of Provisional Patent Application Ser. No. 60/687,490 filed on Jun. 3, 2005.

FIELD OF THE INVENTION

This invention relates to implantable surgical stabilization devices and methods for their use, and particularly to devices that stabilize the cervical spine or other osseous structures.

BACKGROUND

In the field of surgery, it is often desirable to connect adjacent structures or fragments under conditions in which the connected structures or fragments may ultimately fuse together to form a unitary structure.

As an example, spinal surgical fusion is the process of bringing together two or more vertebrae under conditions whereby the vertebrae fuse together to form a unitary member of the spinal column. Cervical spinal fusion is often prescribed for patients suffering from degenerative disk disease (whose symptoms include neck pain of discogenic origin with degeneration of the disk confirmed by patient history and radiographic studies), trauma (including fractures), tumors, deformity (indicated by kyphosis, lordosis or scoliosis) pseudoarthrosis, and/or failed previous fusions. In carrying out the procedure, the members must be brought together under conditions that are critically controlled to prevent infection, maintain alignment of opposing members, allow for the stress in the bone that is generated as the healing process matures. Immobilization is an important requirement during this healing process.

The process of bone healing has been widely studied in the prior art. Microfractures, once thought to be negative events, are now seen as part of the natural process of bone remodeling and occur within bone in the course of everyday wear and tear.

Such microfractures are healed by ongoing bone remodeling, which occurs in humans in 120 day cycles. In the early stage of these cycles, bone resorption is first accomplished by osteoclasts. This is followed by new bone formation by osteoblasts over the latter part of each cycle.

Osteoblasts serve a critical role in new bone formation, filling in the bony cavity in areas of bone remodeling with bone matrix. The action of osteoblasts is triggered by parathyroid hormone, and is further regulated by thyroxines under the influence of such growth factors as interleukins (1, 6, 11), insulin-like growth factors, and transforming growth factor-B. Osteoblasts are further known to release cytokines to attract osteoclasts.

Osteoclasts serve to release proteases, which act to dissolve bone mineral matrix, collagen, and clear away damaged bone. Osetoclasts also release matrix-bound growth factors and may serve as a chemoattractant for osteoblasts.

Thus, the process of bone healing is now seen as a continual cycle, in which the body's response to microfractures and stress injuries within healing bone actually serve to strengthen healing ultimately and produce more solid bone. Therefore, a plating system to repair bone fractures or to stabilize separate bony structures and allow them to fuse into a single item is enhanced if it can incorporate or harness the elements of the natural bone healing process.

A common approach for the surgical management of cervical disk disease is anterior cervical spinal fusion. The procedure for anterior cervical spinal fusion is initiated by incising a small opening in the front of the neck. There is minimal trauma to the neck tissues. The damaged disk and/or bone spurs are removed anterior to the spinal cord. This approach allows for minimal spinal or cord traction and therefore a quicker recovery period. Frequently, if there is significant spinal cord compression or if there is more than one disk level involved, a small plate is affixed on the anterior surface of the cervical vertebrae to provide greater permanent stability. If a cervical fusion is done, a surgical collar is prescribed to be worn for several weeks following surgery for further stabilization of the neck during recovery.

According to the present art, the plates commonly used for cervical spinal fusion are fabricated from titanium sheets with holes through which screws are inserted to secure the plate to the bodies of neighboring vertebrae. These plates sometimes have an opening in their central portions that enables the surgeon to view the bone graft between neighboring vertebrae (where fusion has been introduced) to ensure that the plate is maintained in alignment as the plate is fixated to the involved vertebrae by screws.

The anterior cervical fusion process as described above has certain inherent risks that endanger success of the operation. It has been recognized that osseous trans-differentiation during the course of bone healing may have a significant role in improving the structural integrity of healed bone following surgery or trauma. The process of bone remodeling following surgery or trauma may, however, result in partial extrusion of the bone plug or screws placed during surgery to fix the position of bones or fragments if the fusion does not take place.

The potential for post-operative screw extrusion has long been a matter of clinical concern. Various locking devices have been described in efforts to hold the surgical screws in place and prevent their extrusion. However, a situation where the surgical screws are, in fact, locked into position may be undesirable. By preventing any degree of post-operative motion by a single screw, mechanical stress may be displaced onto the entire plate and the attached vertebrae, potentially fracturing the plate or allowing the entire plate to become displaced and dysfunctional.

Furthermore, preventing a certain amount of screw transition to occur following implantation impedes trans-differentiation and the formation of stronger new bone within the healing bone. It is therefore deemed desirable according to the present invention to allow at least a certain amount of beneficial post-operative stabilization plate and screw motion, and to prevent a situation where a screw is locked or otherwise firmly secured in its fully-threaded location following insertion.

SUMMARY OF THE INVENTION

It is an object of this invention to provide a device and system to establish and maintain bone stabilization and enhance post-operative healing in a surgical site, such as the cervical spine of a patient. It is contemplated that the implantation of such a device and system be a part of a surgical procedure for treatment of herniated disks, osteophytes (spurs, arthritis), fractures, or other surgical interventions in which enhanced post-operative stabilization of the cervical spine is desired.

It is further contemplated that such a device and system might be employed in various embodiments for the post-operative stabilization of other anatomic situations, such as the treatment of fractures, surgical osteotomies, or other surgical procedures in which such stabilization and healing are desired.

It is a further object of the invention to provide a plating system with a shielding frame that will allow surgical fasteners, such as bone screws, to transition or extrude at least partially following their surgical placement, while at the same time hold the surrounding tissue, muscles, or other structures away from the screw channel in the plate and prevent tissues from prolapsing into the channel and reducing the freedom of motion that is beneficial to the healing process.

It is a further object of the invention to provide a plating system wherein the egress of a surgical fastener, such as a bone screw, is met at a certain point with a predetermined and variably increasing resistance, without locking or firmly securing said screws in their original surgical locations.

It is a further object of the invention to provide a plating system that provides for post-operative transition, i.e., egress and ingress, of a surgical fastener, such as a bone screw, without locking or firmly securing said screws in their original surgical locations.

It is a further object that the device be characterized as causing minimal tissue irritation or injury to adjacent anatomic structures, such as the trachea, esophagus, blood vessels, nerves, and other anatomic structures when employed for anterior cervical stabilization.

It is another object of the invention to provide a plating system that conforms to the natural anatomy of the patient thereby minimizing extensive decortication and plate bending.

It is another object to provide a plating system that permits a wider visualization of the bone graft than plates of the present art thereby improving an ability to align the plate and vertebrae.

It is a further object of the invention to provide a plating system for cervical implantation whose surface is especially treated to promote compatibility at the interface between tissue and plate.

In one embodiment, an observation port enclosed by the plating system provides an unobstructed view of the involved disk area between the vertebrae. In an alternate embodiment, the shielding frame is secured to the plate by disposing one clearance side thereof through the observation port and another clearance side over the first or second attachment side of the plate as described below.

The porous anodized surfaces of the plate and/or shielding frame may be impregnated with an agent that is selected according to the environment required by a specific application. For example, the selection of such an agent may be based on the requirement that the surface be maintained in a sterile condition, in which case, the agent may be an antibiotic.

In another exemplary circumstance the surfaces of the plate and/or shielding frame may have a coating containing an agent selected to promote adhesion of the implant to the tissue, in which case the agent may promote the formation of mineralized tissue at the interface.

In yet further exemplary applications according to the present invention, the porous anodized surfaces of the plate and/or shielding frame may be impregnated with two or more agents that are selected according to the environment required by the application. In such applications, the agents may be provided in combination, in layers, or in specified regions on or within the plate and/or shielding frame.

These and other objects of the present invention will be apparent to one skilled in the art upon reading the present disclosure of the invention.

BRIEF DESCRIPTION OF THE DRAWINGS

FIGS. 6A and 6B show the top view, FIGS. 6C and 6D show the side view, and FIG. 6E shows the bottom view of the exemplary plating system with the rotating pivotal shield attached.

DETAILED DESCRIPTION

Figure 1A:
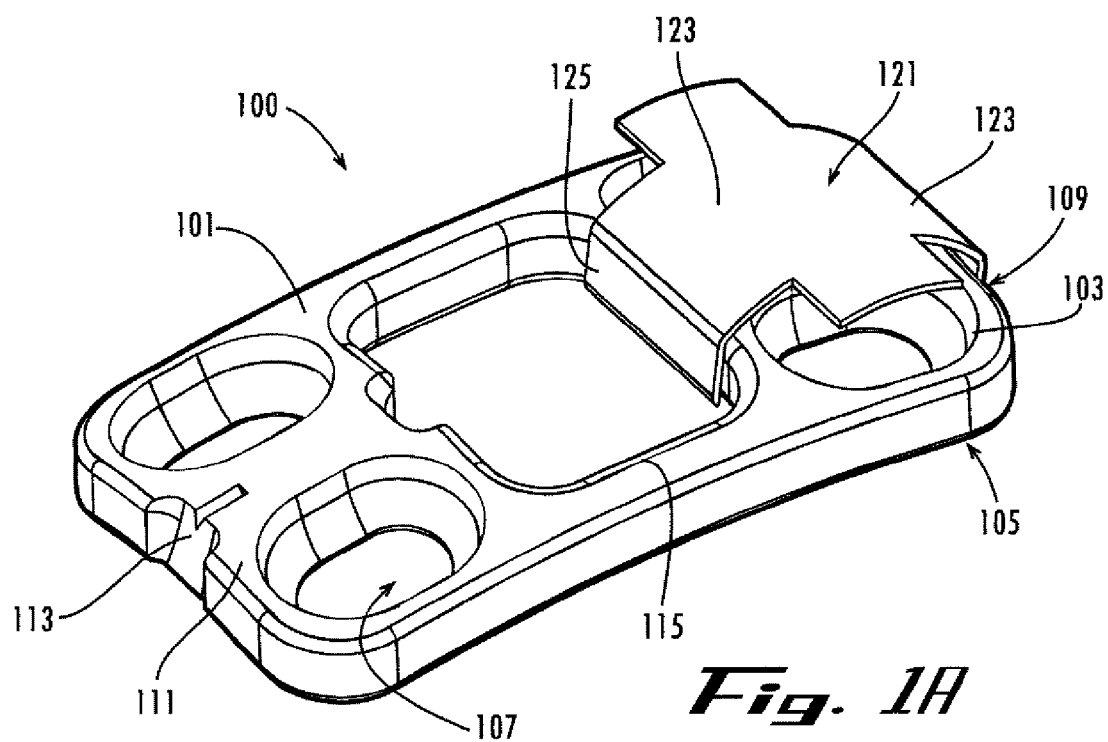
FIGS. 1A, 1B, and 1C show an exemplary plating system with a shielding frame attached to an anterior cervical plate according to the present invention.

The present invention provides a surgically implantable tissue stabilization plating system comprising a plate having a plurality of apertures therethrough for receiving surgical fasteners, and one or more receptors on the plate for securing at least one shielding frame thereto. In certain preferred embodiments, the plate according to the present invention has at least two apertures for receiving self-tapping surgical screws that extend through the thickness of the plate and are screwed into the body of the vertebrae or other underlying bone. The shielding frame is preferably secured to the plate at the receptors such that when the surgical fasteners are initially implanted in the tissue in an operable position, there is no direct force of contact between a surgical fastener, such as a screw head, and the shield frame, which would otherwise impede egress of the fastener in response to physiological stresses of the anchored tissue. Therefore, the invention provides an advantageous degree of permitted egress and ingress of the surgical fasteners which facilitates beneficial tissue remodeling and appropriate healing for a physiologically dynamic environment.

The plating system and shielding frame according to the present invention allows at least partial unimpeded extrusion of one or more underlying surgical fasteners, which also provides the benefit of shielding a partially extruded fastener, such as a screw head, from undesirable prolapsing contact with adjacent tissues, such as muscle or esophageal tissue. Therefore, the system of the present invention minimizes obstruction of free movement of the fasteners and plate, which is beneficial to the healing process and further protects against erosion of adjacent tissues or anatomic spaces.

A shielding frame according to preferred embodiments of the present invention does not contact any of the surgical fasteners at the time the device is implanted, and does not serve to lock or prevent reverse motion of the fasteners following their surgical placement. The shielding frame according to preferred embodiments of the present invention is constructed of a flexible material, such that if a fastener does egress to the point of contact with the shielding frame, it permits a selectively increasing degree of resistance on egress of the surgical fastener, as well as increasingly encouraging ingress of the fastener. In certain embodiments, the flexible material is a band of metal constructed of an alloy and thickness depending upon the resistance desired for the anatomical location and condition of the patient. Therefore, the system and shielding frame of the invention permit selectively variable motion of the surgical fasteners to facilitate stress relief and tissue remodeling during healing.

The present invention provides a surgical stabilization device, comprising a plate having a thickness, a width, a first attachment end, a second attachment end, a length defined between said first and second attachment ends, and one or more apertures extending through the thickness of said plate to receive a respective one or more surgical fasteners placed therethough. The device also comprises one or more surgical fasteners and one or more selectively securable shielding frames, which are disposable in either a first position or a second position.

When a shielding frame is disposed in the first position, it allows unencumbered placement and implantation of one or more of the surgical fasteners through one or more of the respective apertures in the plate. When the shielding frame is disposed in the second operative position it is secured on the plate to allow at least limited post-operative extrusion of at least one surgical fastener. Advantageously, the implanted shielding frame in the second position thus permits associated tissue movement and translational response effecting beneficial remodeling.

In preferred embodiments, the tissue is bone and the surgical fasteners are bone screws. In preferred embodiments, the length of the device is sufficient to extend from one vertebral body across one intervertebral space to an adjacent vertebral body. In other preferred embodiments, the length of the device is sufficient to extend from one vertebral body across two or more intervertebral spaces to an adjacent vertebral body.

In certain embodiments of the invention, the shielding frame is freely detachable from said plate in said first position. In alternate embodiments, the shielding frame is movably attached to said plate, such that said first position allows unencumbered placement of one or more surgical fasteners through one or more of the apertures in said plate, and further disposed when secured in said second position to allow at least limited post-operative extrusion of at least one surgical fastener and associated tissue movement effecting beneficial remodeling.

In some preferred embodiments, the plate contains one or more receptacle detents in the sides thereof to allow secure attachment of the shielding frame in its second position. The shielding frame can be further secured to the plate with the use of additional fasteners or adhesives.

The present invention also provides a shielding frame for a surgical stabilization plate, wherein the shielding frame comprises a body, clearance sides, and one or more retention tabs selectively securable to at least one receptacle on the stabilization plate attached to an anatomic structure by at least one surgical fastener. The secured shielding frame is preferably disposed above the fastener on the stabilization plate to eliminate resistance to the initial egress of the fastener, and preferably to provide a physical space between the shielding frame and the fastener.

In preferred embodiments, the body of the shielding frame comprises a band of shape-memory material of a pre-determined thickness. The shielding frame is capable of being utilized in a first or second position, such that said shielding frame may be disposed in the first position to allow unencumbered placement of one or more surgical fasteners through one or more of the apertures in said plate, and further disposed when secured in said second position to allow at least limited post-operative egress or ingress of at least one surgical fastener. Selection of the resilience properties and shape of the body will determine the increasing level of resistance to determine the rate of fastener egress and the aptitude for fastener ingress, depending upon the circumstances and desired outcome. In preferred embodiments, the body of the shielding frame further comprises one or more lateral wings to shield adjacent anatomical structures from prolapsing into contact with the fastener when secured in said second position.

In preferred embodiments, the shielding frame is a pivotal shield rotatably attached to the plate by a post/rivet therethrough defining a pivoting axis. The rivet of the rotating pivotal shield passes through the stabilization plate and is secured in this version by a flaring of the end of the rivet. The body of the rotating pivotal shield of the present invention can be rotated in any position, depending upon the circumstances and desired outcome, for instance, to either provide access to the screws for implantation and adjustment or to remain above and shield the screws after implantation. In preferred embodiments, the rotating pivotal shield of the present invention can be permanently attached to the plate. In another preferred embodiment, the edge of the rotating pivotal shield remains above the screws, leaving a space between the edge of the rotating pivotal shield and the heads of the screws when implanted to permit movement of the screws postoperatively and functionally improved movement of tissue to promote translational response and healing remodeling, as well as protecting adjacent tissues from erosion otherwise caused by extruding fasteners.

The invention further provides methods of stabilizing two or more anatomic structures for healing, comprising the steps of: implanting a plate by securing the plate to the anatomic structures using one or more surgical fasteners each placed through an aperture in the plate; and securing one or more shielding frames to the plate, such that the frame at least partially protects the surgical fastener from contact with adjacent tissues, and wherein the frame provides no effective resistance to egress of the fastener to permit associated tissue movement effecting beneficial remodeling.

The invention provides further methods of stabilizing two or more anatomic structures for healing and implanting the devices as described above and more fully below.

Figure 1B:
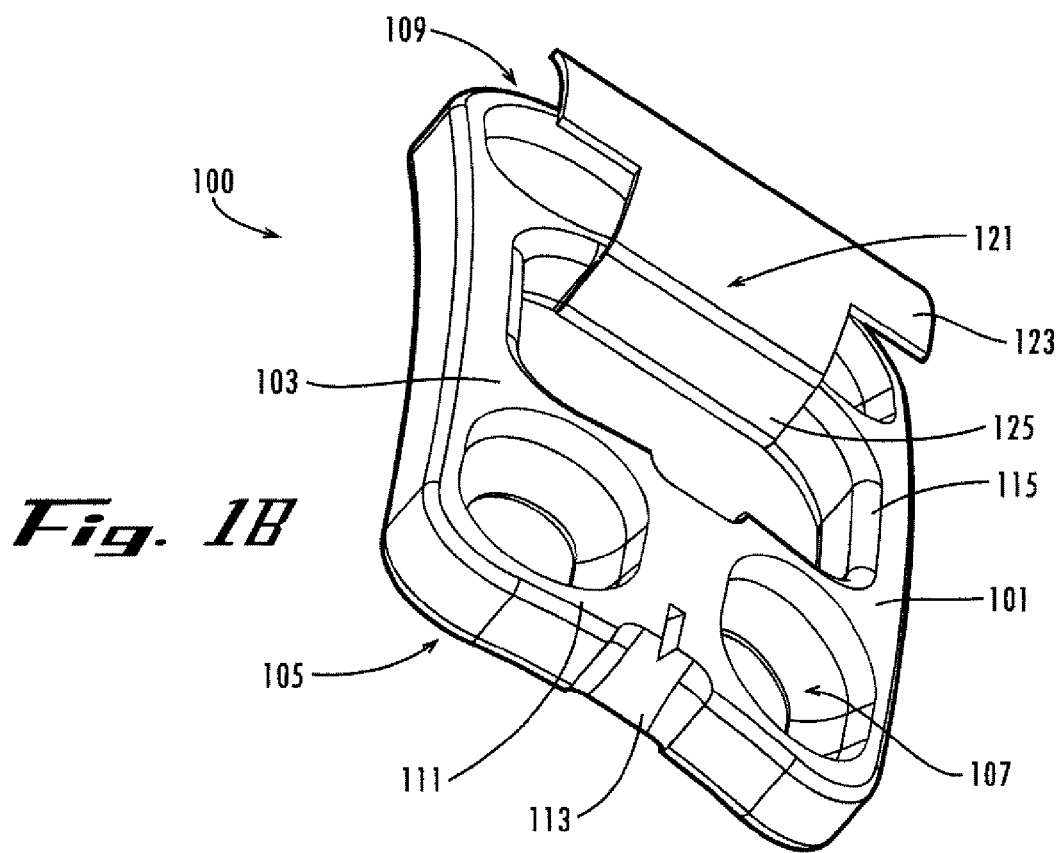
Figure 1C:
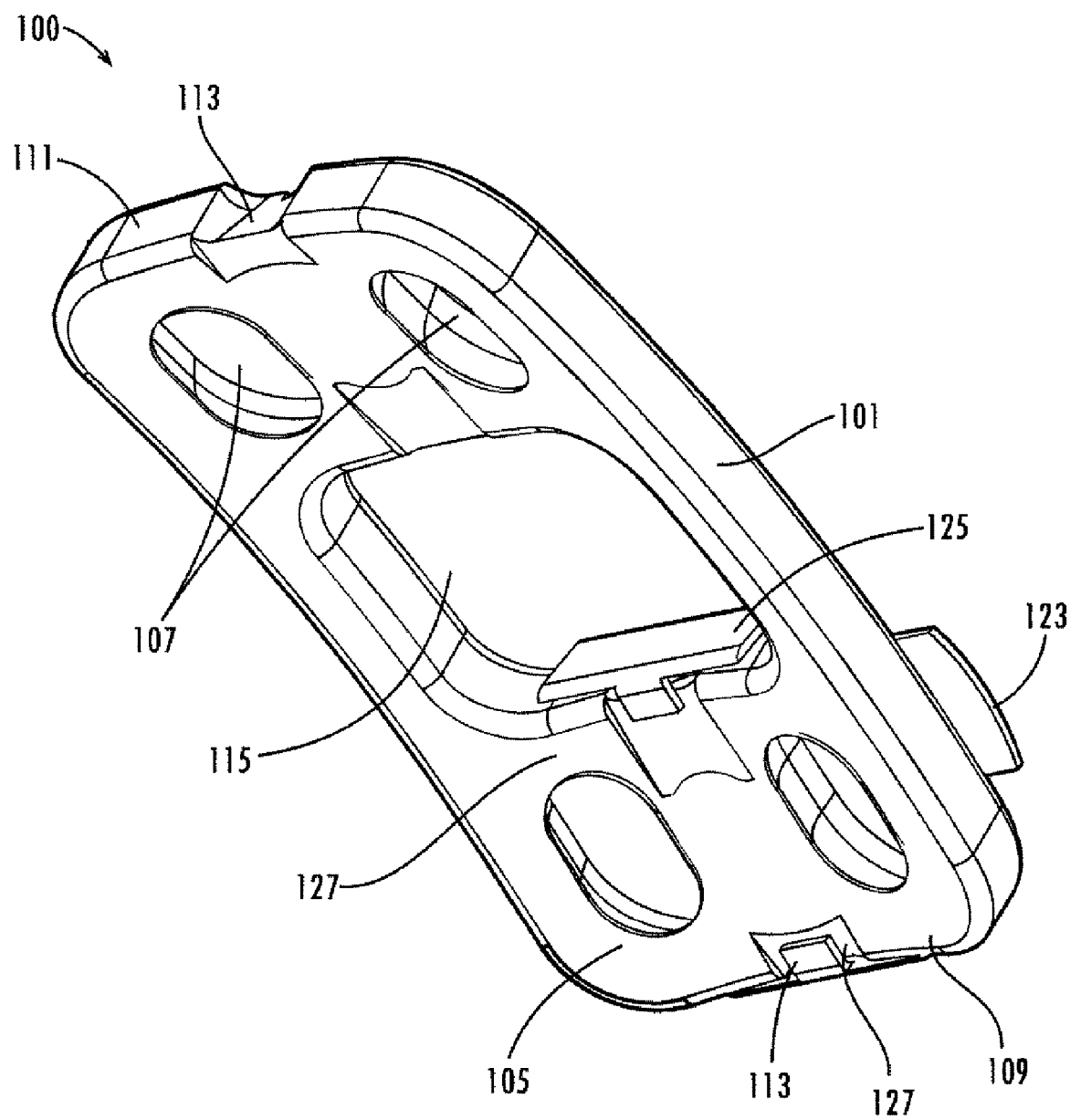

Turning now to a discussion of the drawings, FIGS. 1A, 1B, 1C, are views of an exemplary plating system assembly 100 according to the present invention, consisting of a plate 101 and a shielding frame 121. As shown in this example, the plate 101 has a first attachment end 109, a second attachment end 111, an outer surface 103, an inner surface 105, a plurality of apertures 107 to receive surgical screws or other fasteners (not shown), an observation port 115, and one or more retention detents 127. The apertures 107 are preferably elongated to permit a limited range of motion to the implanted plate to promote beneficial translation during healing.

The shielding frame 121 as shown in FIGS. 1A-1C is a band-like structure fabricated of metal or other spring-like materials which may have one or more lateral wings 123, clearance sides 125, and retention tabs 113. The shielding frame 121 is designed to allow a limited range of motion to the implanted plate for subsequent partial screw extrusion to further promote beneficial translation during healing.

In use as an example, the cervical plate is first attached to adjacent vertebrae with surgical fasteners by an operator. Surgical screws are a commonly used surgical fastener, but the use of other surgical fasteners such as wires, pins, clips, sutures, or other surgical fasteners is also contemplated by the present invention. Following satisfactory placement of the plate, one or more shielding devices are attached to each plate at the discretion of the operator to allow for limited fastener and plate motion and to shield the adjacent tissues and structures such as the esophagus, trachea, blood vessels, or nerves from potential erosion or pressure from a postoperatively extruded screw.

In the exemplary embodiment shown in FIGS. 1A-1C, the shielding frame 121 snaps onto an implanted plate 101 and is retained by frictional pressure of the retention tabs 113 of the shielding frame 121 within the retention detents 127 of the plate 101. As can be seen in FIGS. 1A-1C, one or more separate shielding frames may be attached to the plate 101 according to the present invention. A shielding frame can alternatively be attached to the plate with one or more surgical fasteners. Also shown in the secured position of the shielding frame 121 on the plate 101 in FIGS. 1A-1C, a space is present between the shielding frame 121 and the heads of the screws (not shown) when implanted to permit movement of the screws postoperatively and functionally improved movement of tissue to promote translational response and healing remodeling, as well as protecting adjacent tissues from erosion otherwise caused by extruding fasteners. Preferred embodiments of the device permit at least 1 to 5 millimeters of unimpeded postoperative screw extrusion. Thereafter, the screw contacts the shielding frame within a range of selectively increasing resistance which dynamically decreases egress and promotes ingress of the screw.

In yet other embodiments according to the present invention, the shielding frame may be movably attached by a hinge or other motile attachment device to one side of the plate, and may be moved from an open configuration during placement of the plate to a closed secured configuration at the conclusion of the surgical procedure to provide its shielding function. Such an embodiment may employ similar retention tabs and detents or other engaging mechanisms to provide continuing shielding of the screws or other fasteners within.

Figure 2:
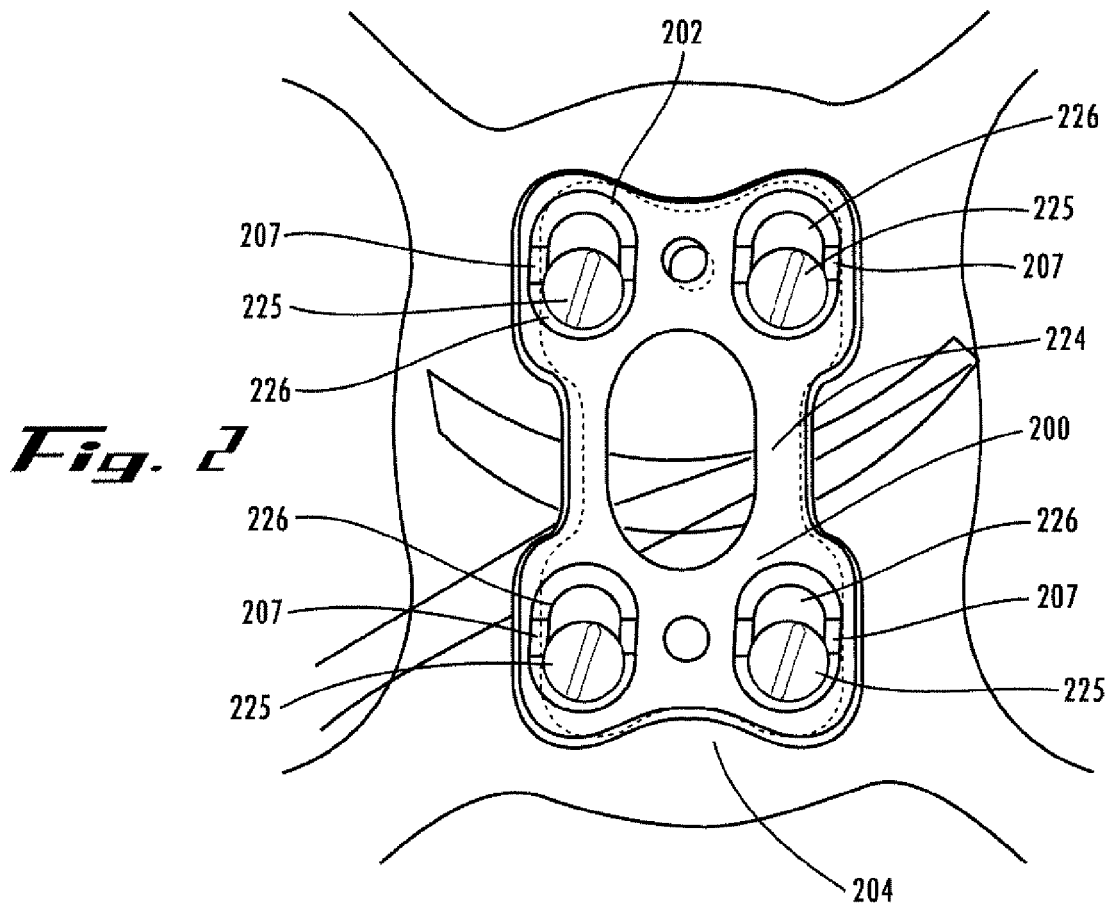
FIG. 2 shows details of an exemplary plate implanted against the anterior surface of the cervical spine, capable of receiving an attachable shielding frame prior to surgical wound closure.

FIG. 2 shows details of an exemplary plate 200 after its surgical implantation on adjacent vertebral bodies of the cervical spine. The plate 200 is capable of receiving an attachable shielding frame (not shown in FIG. 2) according to this invention, and comprises a first attachment end 202, an observation port 224, a second attachment end 204, and shielding frame retention detents 207. The first attachment end 202 and second attachment end 204 contain a plurality of slot-like apertures 226 which receive surgical screws 225 placed therethrough and into predrilled holes in the underlying vertebral bone. The observation port 224 presents a clear unobstructed view of the vertebral bodies permitting any last adjustment of the alignment of the vertebrae if necessary.

The screw apertures 226 are shown in FIG. 2 as slots and are not employed as round bores. The elongated shape of the screw apertures 226 permits a slight amount of slippage of the plate 200 on the surface of the vertebrae bodies. This slippage accommodates the strain that is generated by the vertebrae which occurs as a part of the healing process and allows trans-differentiation to promote the process of bone remodeling, resulting in the potential for superior healing and a structurally stronger resulting union.

Figure 3:
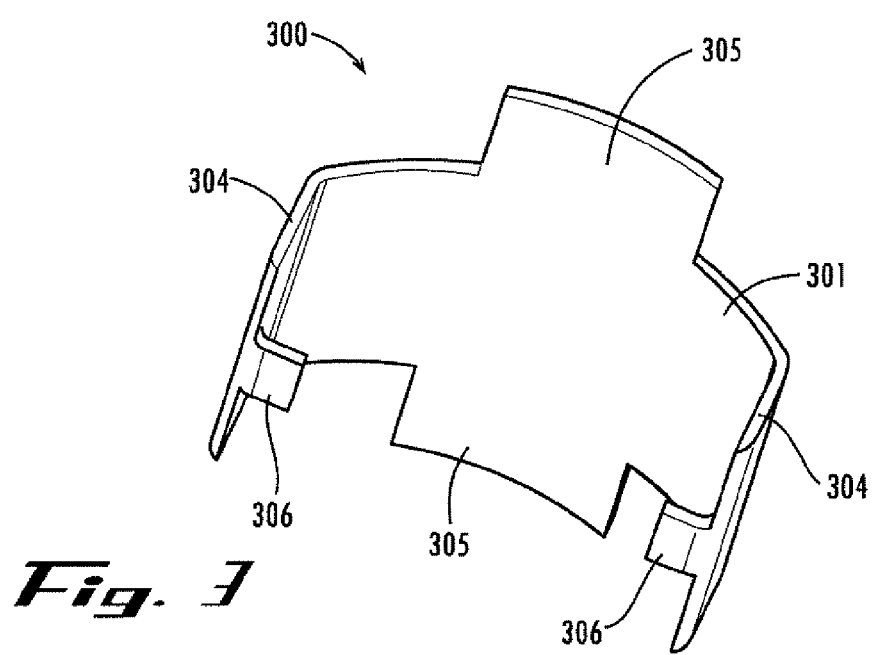
FIG. 3 shows details of an embodiment of an exemplary shielding frame according to the present invention.

A preferred embodiment of a shielding frame 300 according to the present invention is shown in FIG. 3. As shown, the exemplary shielding frame 300 has a memory-retaining band-like body 301 connecting clearance sides 304 which contain retention tabs 306. The body 301 has an inner surface 302 and an outer surface 303, and may have one or more lateral wings 305 for screw shielding. As shown in FIG. 3, the shielding frame 300 is configured to attach to a cervical plate according to the present invention by a spring-like attachment using frictional retention tabs 306 to engage the cervical plate (not shown in FIG. 3). In alternate preferred embodiments according to the present invention, a shielding frame may be hinged or otherwise movably attached to a portion of a cervical plate, and capable of being moved from an open position to a closed position to engage the plate and provide its shielding function to shield adjacent tissues from extruding screws beneath the shielding frame. In all embodiments according to the present invention, the shielding frame and clearance sides are configured to prevent initial direct force between the shielding device and the head of underlying surgical screws, or to otherwise avoid any locking action or other effects that would prevent at least some unimpeded, improved functional degree of post-surgical displacement motion by the screw or screws contained therein.

The invention contemplates embodiments of the shielding frame that are secured in a transverse position to detents in the sides of the plate, or alternatively a shielding frame which traverses the entire plate from end to end or side to side. Other embodiments contemplated by the present invention include plates with detents located for transverse or longitudinal attachment of one or more shielding frames.

Figure 4:
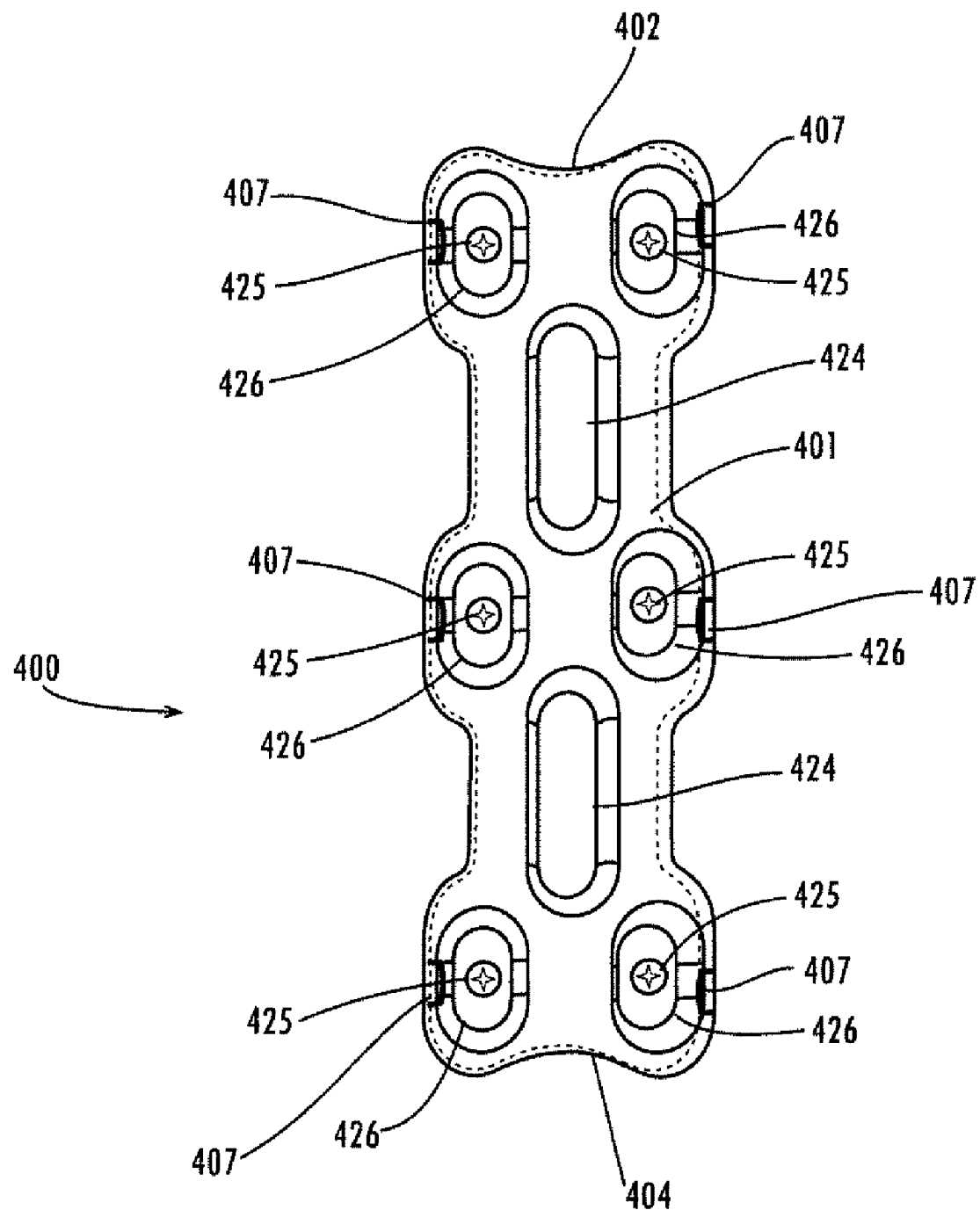
FIG. 4 shows an embodiment of a two level plating system according to this invention.

Another embodiment according to the present invention is shown in FIG. 4, where a plating system assembly 400 is designed to cover two levels (two disk regions). The exemplary plate 401 as shown comprises a first attachment end 402, two observation ports 424, a second attachment end 404, and shielding frame retention detents 407. The exemplary plate 401 as shown further has multiple apertures 426 located to insert corresponding multiple screws 425 into one vertebral body, another set of apertures 426 for inserting screws 425 into a neighboring vertebral body, and yet a third set of apertures 426 for inserting screws 425 into a third vertebral body. The exemplary plate 401 as shown may be further provided with one or more retention detents 407 to permit the attachment and retention of shielding frames (not shown in FIG. 4) at one or more apertures in a transverse and/or longitudinal fashion. Other embodiments according to the present invention may have other pluralities of apertures for other applications requiring surgical stabilization of underlying structures.

Figure 5:
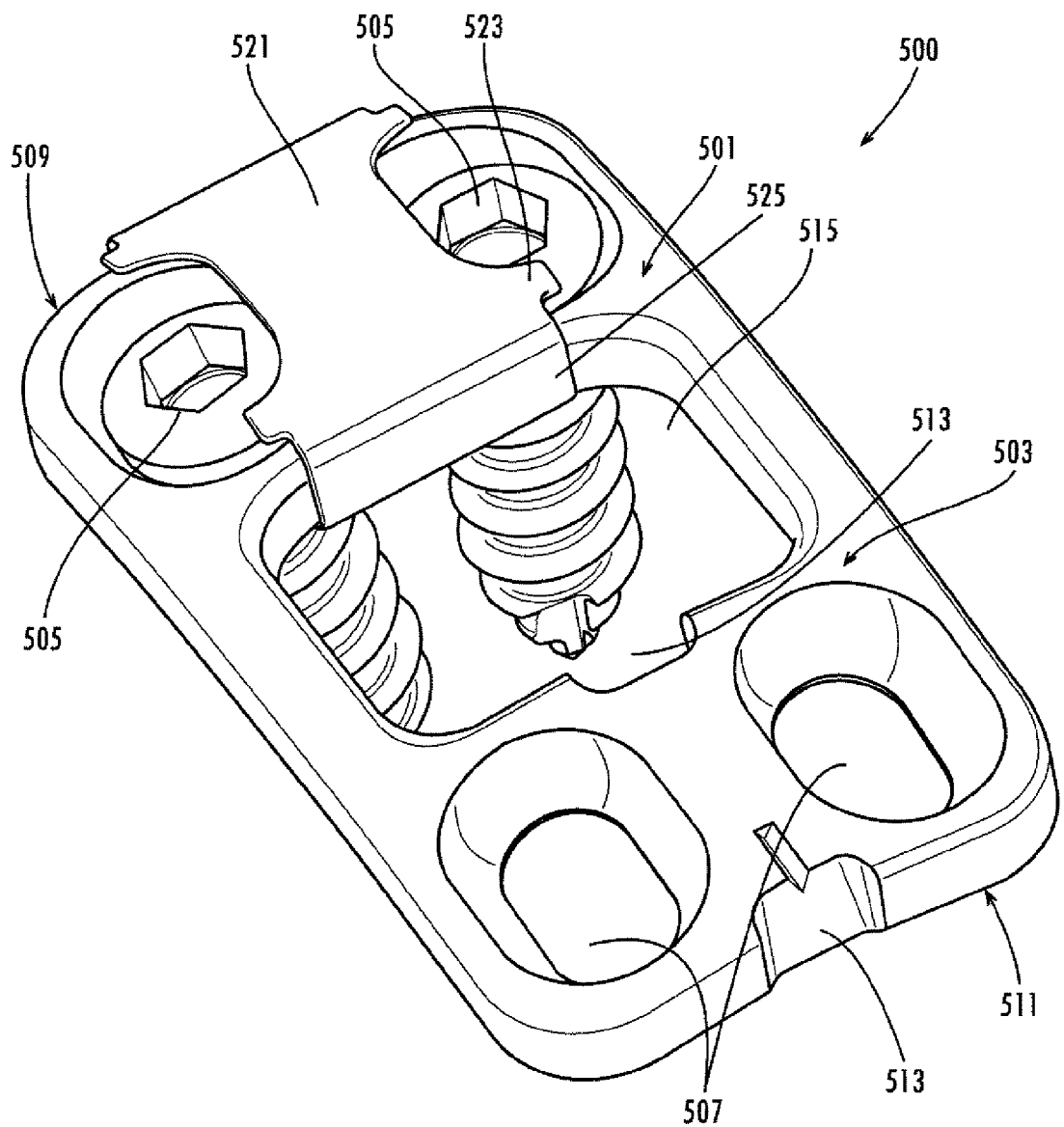
FIG. 5 shows an alternate embodiment of an exemplary plating system with a shielding frame attached to an anterior cervical plate according to the present invention, with an alternately configured shielding frame.

FIG. 5 shows an alternate exemplary plating system assembly 500 according to the present invention, consisting of a plate 501 and a shielding frame 521. As shown in this example, the plate 501 has a first attachment end 509, a second attachment end 511, an outer surface 503, an inner surface (not shown), a plurality of apertures 507 to receive surgical screws or other fasteners 505, an observation port 515, and one or more retention detents 513. The shielding frame 521 as shown in Figs. 1A-1C is a band-like structure fabricated of metal or other spring-like materials which may have one or more shielding tabs 523, clearance sides 525, and retention tabs (not shown). Also shown in FIG. 5, a space is present between the shielding frame 521 and the screws 505 in the secured position with the shielding frame 521 attached to the plate 501 when implanted to permit movement of the screws postoperatively.

Figure 6A:
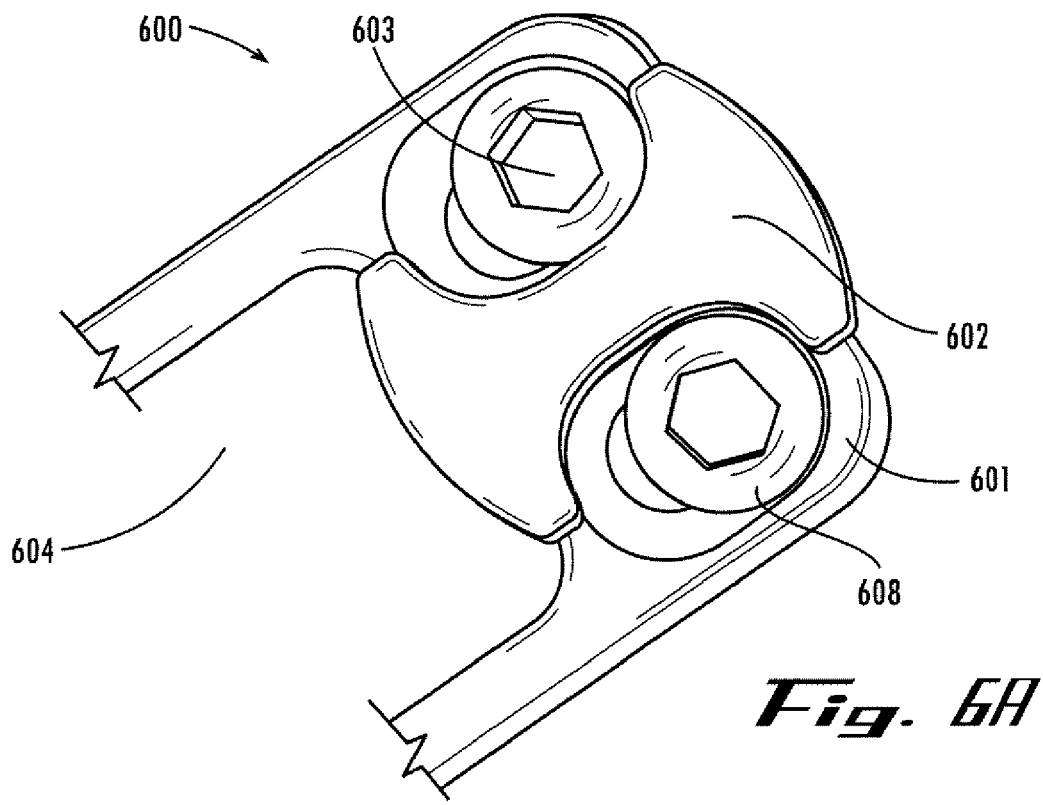
FIGS. 6A, 6B, 6C, 6D, and 6E show an alternate embodiment of an exemplary plating system with a rotating pivotal shield rotatably attached to an anterior cervical plate by a rivet on the bottom of the shield that passes through the plate and is secured by a flaring of the end of the rivet according to the present invention.
Figure 6B:
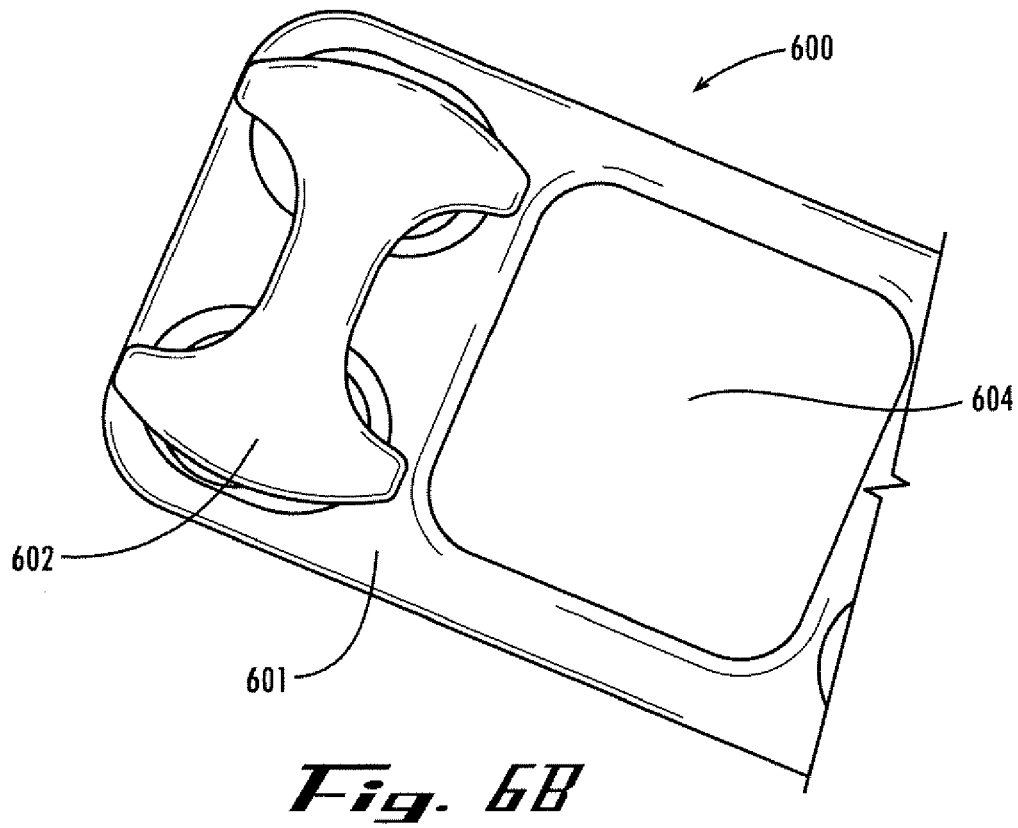

FIGS. 6A, 6B, 6C, 6D, and 6E show an alternate embodiment of an exemplary plating system assembly 600 with a rotating pivotal shield 602 attached according to the present invention. FIGS. 6A and 6B show the top view of the exemplary plating system assembly 600, consisting of a plate 601 and a rotating pivotal shield 602 attached to the plate 601. The rotating pivotal shield 602 is placed in either a position that exposes the heads 608 of the screws 603 for implantation or adjustment (FIG. 6A), or partially or completely shielding the screws 603 (FIG. 6B) for postoperative indwelling. Also shown in FIGS. 6A and 6B is an observation port 604 which presents a clear unobstructed view of the vertebral bodies permitting adjustment of the alignment of the vertebrae, if necessary.

Figure 6C:
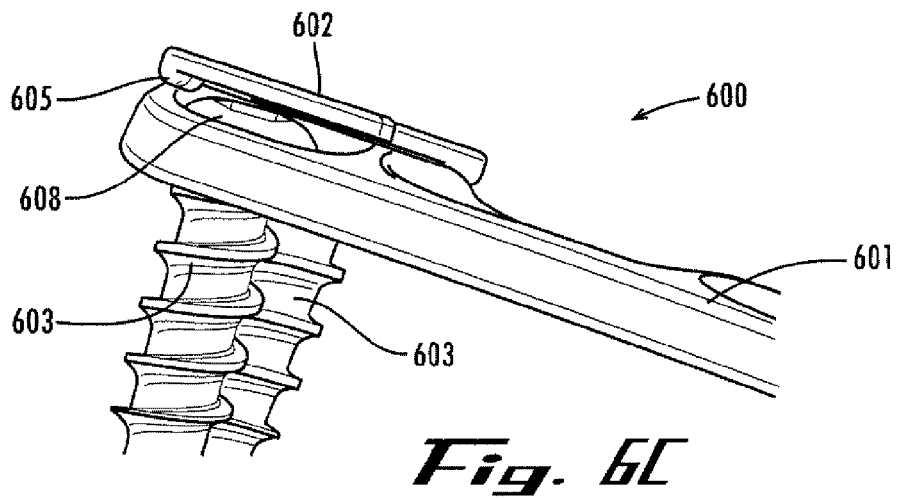
Figure 6D:
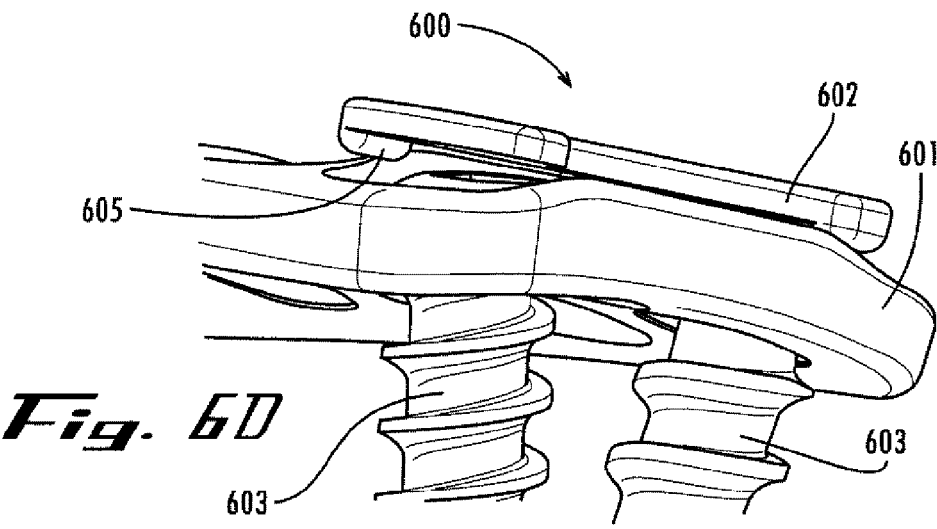

FIGS. 6C and 6D show the side view of the exemplary plating system assembly 600 with a rotating pivotal shield 602 attached according to the present invention. As shown in this view, the rotating pivotal shield 602 is attached to the plate 601 via a rivet 607 (not shown in FIGS. 6C and 6D), defining a rotational axis, mounted on the bottom of the shield and positioned between two screws 603. The body of the rotating pivotal shield 602 remains above the screws 603 so that a space is present between the rotating pivotal shield 602 and the screw head 608 in the secured position when implanted to permit movement of the screws postoperatively. Furthermore, the shield 602 is equipped with retention flanges 605 which engage an aspect of the plate 601 (e.g., edges or screw apertures) for frictionally maintaining the shield 602 in an orientation for either implantation or indwelling.

Figure 6E:
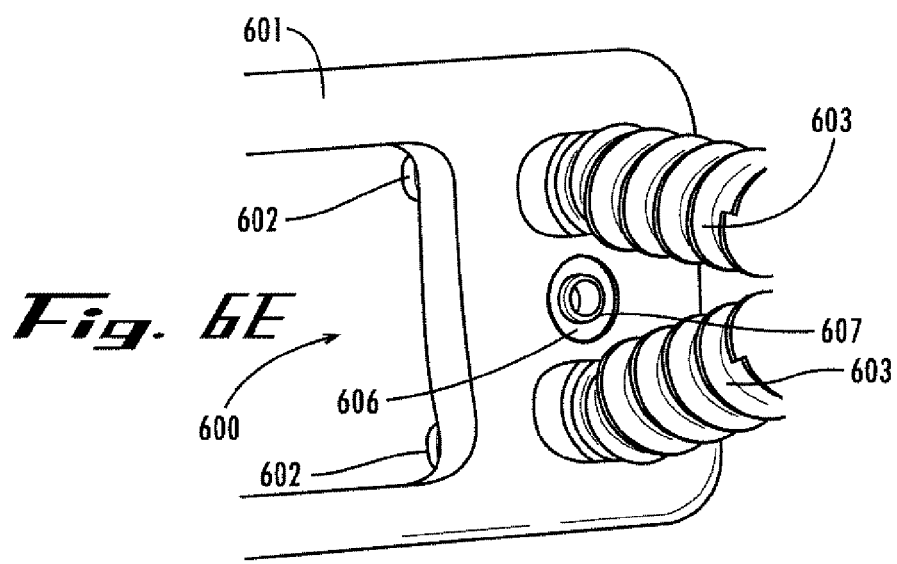

FIG. 6E shows the bottom view of the exemplary plating system assembly 600 with the rotating pivotal shield 602 attached according to the present invention. As shown in this view, the rivet 607 located in the middle between the screws 603 passes through the plate 601 and is secured in this version by a flaring 606 of the end of the post/rivet 607.

In various preferred embodiments according to the present invention, a preferred material for fabricating a plate, shielding frame, rotational posts/rivets and/or screws for anterior cervical fusion is titanium because of its resistance to corrosion. Other preferred materials for the fabrication of such plates and screws include, but are not limited to, anodized titanium, stainless steel, other metals and metal alloys, ceramics, rigid plastics and other polymers, and combinations thereof.

In various preferred embodiments according to the present invention, the plate, shielding frame, and/or screws may be fabricated of titanium with porous anodized surfaces. The porosity of an anodized surface varies according to the composition and temperature of the anodizing solution, and the anodizing voltages. In general, titanium and aluminum surfaces anodized in solutions of sulfuric or phosphoric acids produce porous oxide surfaces. Titanium or aluminum surfaces anodized in weaker acids (e.g., boric, oxalic or organic acids) are non porous.

A preferred anodizing process is to polish the titanium surfaces electrolytically using known electropolishing solutions and then anodize the surfaces using a solution with sufficient content of an organic acid such as hydrofluoric acid or other acids at a selected voltage and temperature to provide a surface coating having pores that may be receptive to various selected agents.

In another embodiment of the invention, the surfaces of the plate, shielding frame, and/or screws may be porous anodized, with surface pores which are impregnated with compounds that promote various objectives. For example, one such compound may be an antibiotic such as penicillin to prevent infection. Other non-limiting examples of therapeutic compounds include growth factors, hormones or connective agents such as lysine which promote healing of the wound.

In yet further embodiments according to the present invention, shielding frames may be provided to attach to or otherwise be employed in combination with prior art surgical plates or other implants to shield partially extruding screws, other fasteners, implants, or other items and restrict their undesired migration or erosion into other tissue structures or anatomic sites, while at the same time provide a range of motion for the fasteners and stabilization plates under selective resistance to promote egress and ingress of the fasteners and beneficial tissue remodeling under normal physiological pressures.

Variations and modifications of this invention may be contemplated after reading the specification and studying the drawings which are within the scope of this invention. While the above is a complete description of the preferred embodiments of the present invention, various alternatives, modifications, and equivalents may be used. Therefore, the above description should not be taken as limiting the scope of the invention, which is defined by the following claims.

EXAMPLES

Example 1

Implantation of a Surgical Stabilization Device Using a Clip-on Shield

A transverse anterior cervical incision is made and the underlying tissue is dissected to laterally displace the trachea, esophagus, blood vessels, muscles, and major neural structures to expose the face of anterior cervical vertebrae at the desired level. The disease cervical disk is then removed, and a bone graft is inserted into the intervertebral space. This bone graft may be an autograft, using bone obtained from the same patient (e.g., hip graft) or an allograft (bone obtained from a bone bank from a cadaver) or a surgical spacer with bone material inside. The patient's own bone will grow into the bone graft and incorporate the graft bone as its own. This process creates one continuous bone surface and eliminates motion at the fused joint. To support the healing graft, and to further promote bone healing, a plate is placed to support the vertebrae to be fused. Using a template, holes are predrilled into the vertebral bodies above and below the fusion site. A plate according to the present invention is then placed and secured with bone screws inserted through the slotted apertures of the plate. One or more shielding frames according to the present invention are then attached to detents in the plate, with the bands of the shielding frames extending above, but not in contact with the implanted screws to allow for at least some postoperative motion by the screws. The shielding frames serve to allow such motion for its beneficial translational effect in the course of bone remodeling and healing. The shielding frames further protect adjacent structure such as the esophagus, blood vessels, or trachea from erosion or other injury from partially extruding screws postoperatively.

Example 2

Implantation of a Surgical Stabilization Device Using a Rotating Pivotal Shield

A transverse anterior cervical incision is made and the underlying tissue is dissected to laterally displace the trachea, esophagus, blood vessels, muscles, and major neural structures to expose the face of anterior cervical vertebrae at the desired level. The disease cervical disk is then removed, and a bone graft is inserted into the intervertebral space. This bone graft may be an autograft, using bone obtained from the same patient (e.g., hip graft) or an allograft (bone obtained from a bone bank from a cadaver) or a surgical spacer with bone material inside. The patient's own bone will grow into the bone graft and incorporate the graft bone as its own. This process creates one continuous bone surface and eliminates motion at the fused joint. To support the healing graft, and to further promote bone healing, a plate is placed to support the vertebrae to be fused. Using a template, holes are predrilled into the vertebral bodies above and below the fusion site. A plate according to the present invention having a rotating shield is then placed and secured with bone screws inserted through the slotted apertures of the plate. The shield is then rotated 90° to engage retention tabs with the screw apertures and lock the shield in place over the screw heads. The body of the rotating pivotal shield extends above, but not in contact with the implanted screws to allow for at least some postoperative motion by the screws. The resulting space between the rotating pivotal shield and the screws serves to allow such motion for its beneficial translational effect in the course of bone remodeling and healing. The rotating pivotal shields further protect adjacent structure such as the esophagus, blood vessels, or trachea from erosion or other injury from partially extruding screws postoperatively.

We claim:
1. A surgical stabilization device, comprising:
   (a) a plate having a thickness, a width, a first attachment end, a second attachment end, a length defined between said first and second attachment ends, and a plurality of apertures extending through the thickness of said plate to receive a plurality of individually corresponding surgical fasteners placed therethrough;
   (b) a plurality of surgical fasteners; and
   (c) at least one selectively pivotal shield rotatably attached to said plate and providing a space between a respective head of at least one surgical fastener and said at least one pivotal shield when in secured configuration to said plate, wherein the space allows unimpeded post-operative egress of said at least one surgical fastener relative to said plate within the space, and wherein said at least one pivotal shield is rotatably attached to said plate between a pair of the plurality of apertures defining a rotational axis for said at least one pivotal shield therebetween.

2. The device of claim 1, wherein said at least one pivotal shield comprises a top, a bottom, and two edges, and wherein said at least one pivotal shield is rotatably secured to said plate by a rivet extending from the bottom of said at least one pivotal shield, said rivet defining the rotational axis.

3. The device of claim 2, wherein said at least one pivotal shield further comprises at least one retention flange extending from the bottom thereof which selectively engages with said plate to permit selective rotation about said rivet.

4. The device of claim 1, wherein said plurality of surgical fasteners are bone screws.

5. The device of claim 1, wherein said length is sufficient to extend from one vertebral body across one intervertebral space to an adjacent vertebral body.

6. The device of claim 1, wherein said length is sufficient to extend from one vertebral body across two or more intervertebral spaces to an adjacent vertebral body.

7. The device of claim 1, wherein said at least one pivotal shield is rotatably attached to said plate to allow unencumbered placement of one or more surgical fasteners through at least one of the pair of the plurality of apertures in said plate.

8. The device of claim 1, wherein said plate contains one or more detents to allow secure attachment of said at least one pivotal shield.

9. The device of claim 1, wherein the space allows at least limited movement of said at least one surgical fastener relative to said plate.

10. The device of claim 9, wherein the at least limited movement comprises movement in a longitudinal direction defined from approximately said first attachment end to approximately said second attachment end.

11. The device of claim 1, wherein the unimpeded post-operative egress of said at least one surgical fastener is effective in promoting associated tissue movement effecting beneficial remodeling.

12. The device of claim 1, wherein the unimpeded post-operative egress of said at least one surgical fastener is effective in inhibiting erosive contact of adjacent tissues against said egressing fastener.

13. The device of claim 1, wherein said plurality of apertures comprises a plurality of elongated apertures, and wherein said space further allows at least limited movement of said at least one surgical fastener within a respective elongated aperture.

14. A pivotal shield for a surgical stabilization device, comprising a body, wherein said pivotal shield is rotatably securable to a plate joining two or more anatomic structures anchored by a plurality of fasteners, said pivotal shield securable between a pair of said plurality of fasteners defining a rotational axis for said at least one pivotal shield therebetween, and wherein said pivotal shield provides a gap between said body and a head of said plurality of fasteners when in secured configuration to said plate, and at least partially covers said at least one of the plurality of fasteners, to permit unimpeded egress of said at least one of the plurality of fasteners within said gap.

15. The pivotal shield of claim 14, wherein said pivotal shield has a first and second position, such that said pivotal shield disposed in the first position allows unencumbered placement of at least one of the plurality of fasteners through at least one respective aperture in said plate, and said pivotal shield disposed in said second position, said secured configuration, allows at least limited post-operative extrusion of said at least one of the plurality of fasteners.

16. The pivotal shield of claim 14, wherein the gap allows at least limited movement of said plurality of fasteners relative to said plate.

17. The pivotal shield of claim 16, wherein the at least limited movement comprises movement in a longitudinal direction along said plate.

18. The pivotal shield of claim 16, wherein the unimpeded egress of said plurality of fasteners is effective in promoting associated tissue movement effecting beneficial remodeling.

19. The pivotal shield of claim 14, wherein the unimpeded egress of said plurality of fasteners is effective in inhibiting erosive contact of adjacent tissues against said egressing fastener.

20. The pivotal shield of claim 14, further comprising a rivet extending from the bottom of said pivotal shield and secured to said plate, said rivet defining the rotational axis passing through said plate.

21. The pivotal shield of claim 14, further comprising at least one retention flange extending from the bottom of said pivotal shield for selectively engaging said plate to permit selective rotation about the rotational axis.

22. A method of stabilizing two or more anatomic structures for healing, comprising the steps of:
   a. implanting a plate by securing said plate to said anatomic structures using one or more surgical fasteners each placed through a respective one or more apertures in said plate;
   b. rotatably securing at least one pivotal shield to said plate comprising a body between a pair of said one or more surgical fasteners defining a rotational axis for said at least one pivotal shield therebetween, wherein a gap is produced between said at least one pivotal shield and said one or more surgical fasteners, such that said at least one pivotal shield does not contact said one or more fasteners at the time of implantation of said one or more fasteners to permit unimpeded fastener egress within said gap.

23. The method claim 22, wherein said at least one pivotal shield comprises a rivet on the bottom of said at least one pivotal shield, said rivet secured to said plate and rotatably securing said at least pivot shield to said plate.

24. The method of claim 23, wherein said at least one pivotal shield remains above said one or more surgical fasteners, providing a space between said at least one pivotal shield and said one or more surgical fasteners when implanted to permit at least partially unimpeded egress of a respective surgical fastener therebetween, and to inhibit contact of adjacent tissues against said egressing fastener.

* * * * *